United States Patent [19]

Bowen

[11] 4,373,035

[45] Feb. 8, 1983

[54] ISOTONIC MONOMER FORMULATIONS

[75] Inventor: Rafael L. Bowen, Gaithersburg, Md.

[73] Assignee: American Dental Association Health Foundation, Washington, D.C.

[21] Appl. No.: 269,067

[22] Filed: Jun. 1, 1981

[51] Int. Cl.³ .............................................. C08L 33/14
[52] U.S. Cl. .................................. 523/113; 523/116; 524/558
[58] Field of Search ................. 523/116, 113; 524/558

[56] References Cited

U.S. PATENT DOCUMENTS

| | | |
|---|---|---|
| 2,656,277 | 10/1953 | Knappwost . |
| 3,066,112 | 11/1962 | Bowen . |
| 3,179,623 | 4/1965 | Bowen . |
| 3,200,142 | 8/1965 | Bowen . |
| 3,471,927 | 10/1969 | Eisenberg . |
| 3,539,526 | 11/1970 | Bowen . |
| 3,825,518 | 7/1974 | Foster et al. ...................... 260/42.52 |
| 3,835,090 | 9/1974 | Gander et al. ..................... 260/42.15 |
| 3,845,009 | 10/1974 | Gander ............................... 260/42.15 |
| 3,959,212 | 5/1976 | Rocket et al. . |
| 4,080,212 | 3/1978 | Takahashi . |
| 4,102,856 | 7/1978 | Lee . |
| 4,148,988 | 4/1979 | Masuhara et al. . |
| 4,150,012 | 4/1979 | Joos . |
| 4,251,565 | 2/1981 | Bowen . |

OTHER PUBLICATIONS

Nelson et al., "Fluid Exchange in the Margins of Dental Restorations," 44 *JADA* 288 (1952).
Paffenbarger et al., "Direct and Indirect Filling Resins: A Review of some Physical and Chemical Properties," *JADA* 516 (1953).
Misra and Bowen, 61 *J. Coll. Interface Sci.* 14 (1977).
Bowen, "Properties of a Silica–Reinforced Polymer for Dental Restorations," 66 *JADA* 57-64 (1963).
Bowen, 44 *J. Dent. Res.* 895-911 (1965).
Bowen, 58 *J. Dent. Res.* 1101-1107 (1979).
Bowen, 28 (2) *Int'l Dent. J.* 97 (1978).
Bowen, R., "Adhesive Bonding of Various Materials to Hard Tooth Tissues VII, Metal Salts as Mordants for Coupling Agents," in Moskowitz, H., et al. (Eds), *Dental Adhesive Materials*, 205 (1974).
Bowen, 59 *J. Dent. Res.* 809 (1980).
Bowen, 44 *J. Dent. Res.* 1369 (1965).
Brännström et al., "The Dentinal Tubules and the Odontoblast Processes," 30 *Acta Odont. Scand.* 291-311 (1972).
Johnson et al., "Pulp Irritation Due to the Phosphoric Acid Component of Silicate Cement," 29 *Oral Surg.* 447-454 (1970).
Asmussen et al., "The Stability of Water in the Pores of Acid Etched Human Enamel," 36 *Acta Odont.* Scand. 43-45 (1978).
Buonocore, 34 *J. Dent. Res.* 849 (1955).
Buonocore, M., *The Acid Etch Technique* 139 (1975).
Garberoglio et al., "Scanning Electron Microscope Investigation of Human Dentinal Tubules," 21 *Archs. Oral Biol.* 355-362 (1976).
Thomas, "The Extent of the Odontoblast Process in Human Dentin," 58 *J. Dent. Res.* 2207-2218 (1979).

*Primary Examiner*—Joseph L. Schofer
*Assistant Examiner*—Bernard Lipman
*Attorney, Agent, or Firm*—Allegretti, Newitt, Witcoff & McAndrews, Ltd.

[57] ABSTRACT

Application of a composition of matter comprising a solution of water in relatively nontoxic water-stable ethylenically unsaturated monomers, preferably methacrylate and/or acrylate and most preferably methacrylate monomers, which solution is substantially isotonic with normal physiological saline solution. As a further aspect of the invention, the compositions may be prepared by selecting ethylenically unsaturated monomers of varying hydrophilicity or water solubility, equilibrating each such monomer with water to form a two phase system and measuring the concentration of the monomer in the water-rich phase, preparing a mixture of monomers in equilibrium with water such that their cumulative concentration in the water phase is about 0.31 molar, and collecting the monomer-rich phase, which will be saturated with water and will also be isotonic with normal physiological saline.

20 Claims, 1 Drawing Figure

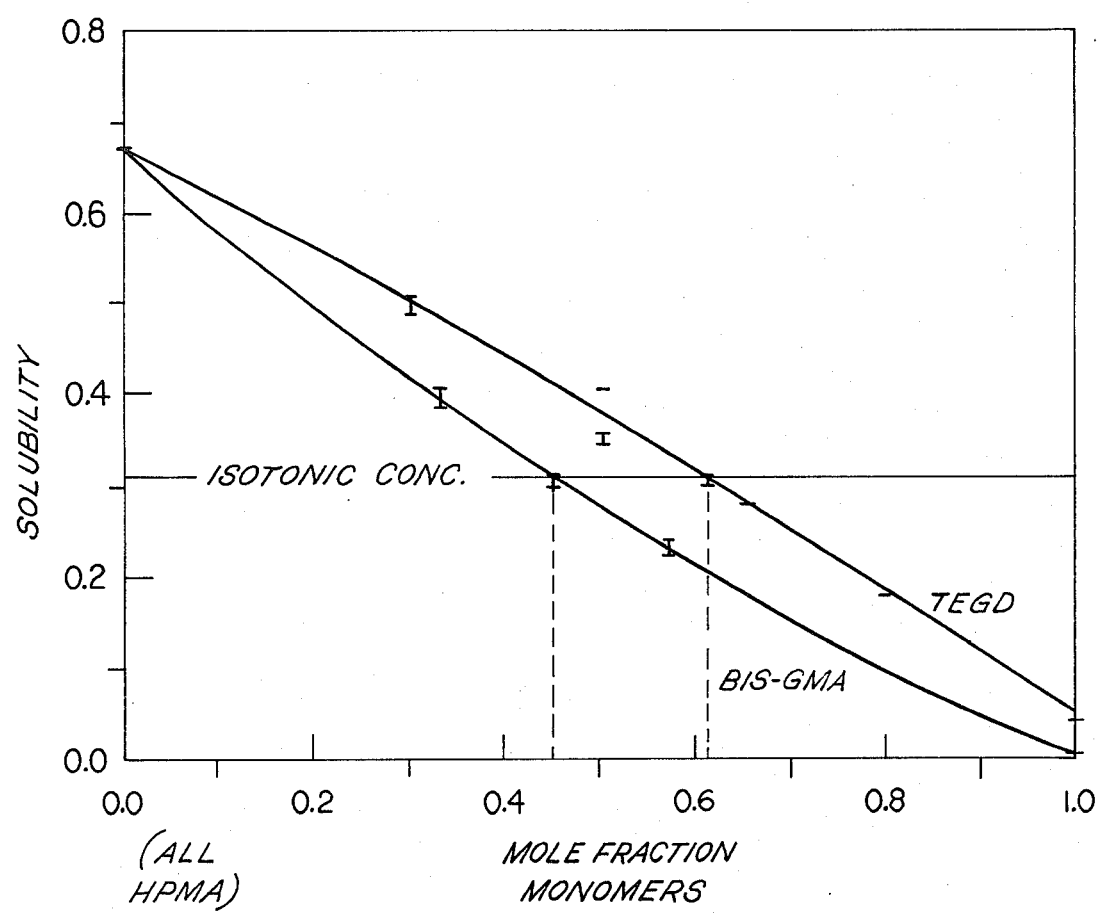

ISOTONIC MONOMER FORMULATIONS

BACKGROUND OF THE INVENTION

1. Field of the Invention

This invention relates to advances in the field of facilitating contact with and adhesion to components of tooth and bone, and especially dentin.

Etching with acids, which is clinically successful in promoting adhesion of reconstructive composite and sealant resins to tooth enamel, see Buonocore, 34 *J. Dent. Res.* 849 (1955), is neither appropriate nor adequate to give bonding of these materials to dentin. Buonocore, M., *The Acid Etch Technique* 139 (1975). Dentin contains much more organic material and water than does enamel, and the concentration, arrangement, and morphology of the hydroxyapatite crystals are also different.

Adhesion of reconstructive synthetic resins to dentin presents difficulties not only because of the nature of dentin as a substrate, but also because of its biological vulnerability. Normal dentin contains a large number of dentinal tubules that extend from the enamel or cementum to the soft tissues of the pulp or root canal. Garberoglio et al., "Scanning Electron Microscope Investigation of Human Dentinal Tubules,"21 *Archs. Oral Biol.* 355-62 (1976). These tubules initially contain portions of vital odontoblasts, the cytoplasm of which extend a fraction of a millimeter peripherally from the pulp. The central and outermost portions of the tubules may contain only fluid or what appears in transmission electron micrographs to be a finely dispersed granular material. Whatever the nature and extent of the odontoblastic processes, there is evidence to support the contention that the health of odontoblasts requires that osmotic and hydrostatic influences on the tubular contents be maintained within certain limits. See Thomas, "The Extent of the Odontoblast Process in Human Dentin," 58 *J. Dent. Res.* 2207-18 (1979), Brännström et al., "The Dentinal Tubules and the Odontoblast Processes," 30 *Acta Odont. Scand.* 291-311 (1972); Johnson et al., "Pulp Irritation Due to the Phosphoric Acid Component of Silicate Cement," 29 *Oral Surg.* 447-54 (1970).

Desiccation of dentin probably destroys local odontoblasts. An air stream can remove water from pores smaller than a certain critical diameter in enamel, and this same principle applies to dentinal tubules provided that the surface tension is not lowered too much by surface-active solutes. Asmussen et al., "The Stability of Water in the Pores of Acid Etched Human Enamel," 36 *Acta Odont. Scand.* 43-45 (1978). This critical diameter is about 1.4 $\mu$m for clean water in hydrophilic capillaries. The critical diameter is smaller if the water contains solutes (proteinaceous material, saliva, etc.) that lower the surface tension. The functional diameters of dentinal tubules can be smaller than this critical size, especially if they contain plugs of smeared surface material or other solids.

The vitality of these odontoblasts, and the pulpal soft tissues with which they associate, should be maintained throughout any procedures designed to restore hard-tooth tissues with adhesive materials. The health of these cells, as indicated, requires the maintenance of their environmental conditions within certain limits, including temperature, pH, osmotic pressure, the absence of toxic solutes, and other factors.

With regard to maintenance of osmotic pressure, odontoblastic cell membranes are believed to have some semipermeability. That is, they can be penetrated readily by water molecules but are relatively impermeable to (or have much lower transport rates for) larger solute molecules and hydrated ions. The present invention is designed to facilitate contacting with and adhesion to the dentinal surface while protecting that surface by neither abstracting water from nor giving up water to the dentin, relative to the normal homeostatic condition of the dentinal and pulpal tissues.

As presently suggested in the literature, the preparation of cut dentin for application of an adhering resin or composite material involves several steps.

Cut dentin starts out with a disturbed or "smeared" surface layer, and dentin that is uncovered by cervical erosion may be covered by a hydrated organic film of salivary pellicle.

These weak surface layers can be substantially removed by a brief exposure (typically 30 seconds; 5 to 120 seconds have been used) to a solution of buffered or unbuffered acids which is isotonic, that is, isosmotic with tissue, having $pK_a$ values between 3.8 and 2.5 and pH values of about 2.5±0.6. Such acids of intermediate strength, for example formic acid, have given no perceptible evidence of pulp irritation in preliminary studies with animals. The pH of such "cleanser" solutions depends upon the $pK_a$ of the acids used and can, therefore, be adjusted independently while maintaining the desired osmotic pressure, which is a colligative property. The effects of various acids have been described. Bowen, 28(2) *Int'l Dent. J.* 97 (1978). See also Bowen, U.S. Pat. No. 4,251,565 and Bowen, Ser. No. 200,989, filed Oct. 27, 1980.

The dentin surface exposed by this acidic cleansing can be provided with improved cationic bonding sites by the brief application of certain metallic salts (such as ferric chloride), called "mordants," in isotonic concentrations. Bowen, R., "Adhesive Bonding of Various Materials to Hard Tooth Tissues VII. Metal Salts as Mordants for Coupling Agents," in Moskowitz, H., et al. (eds.), *Dental Adhesive Materials* 205 (1974); Bowen, 59 *J. Dent. Res.* 809 (1980). See also Bowen, Ser. No. 10,803, filed Feb. 9, 1979, and Bowen, Ser. No. 200,989, filed Oct. 27, 1980. In primates, pulp responses to this treatment also look encouraging.

In both the acid cleaning and mordant application procedures described above, the contents of the dentinal tubules are exposed to aqueous solutions that are isotonic, facilitating maintenance of normal osmotic and hydrostatic pressures.

The next step is the application of adhesion-promoting surface-active comonomers, see Bowen, U.S. Pat. No. 3,200,142; Bowen, 44 *J. Dent. Res.* 1369 (1965), which can bond via chelating groups to the surface-held cations of the substrate and mordant, see Misra and Bowen, 61 *J. Coll. Interface Sci.* 14 (1977), and can also copolymerize with the restorative dental resin applied subsequently. Bowen, "Properties of a Silica-Reinforced Polymer for Dental Restorations," 66 JADA 57-64 (1963); Bowen, U.S. Pat. No. 3,179,623. N-(2-hydroxy-3-methacryloxypropyl)-N-phenylglycine (NPG-GMA) and polyfunctional surface-active comonomers (PolySACs) are examples of such adhesion-promoting surface-active comonomers. Bowen, 44 *J. Dent. Res.* 895-911 (1965); Bowen, 58 *J. Dent. Res.* 1101-07 (1979). See also Bowen, U.S. Pat. No. 4,251,565 and Bowen, Ser. No. 200,989, filed Oct. 27, 1980.

Until now, these comonomers have been applied to the dentin as solutions in acetone or alcohol because they were not sufficiently soluble in monomers such as BIS-GMA and its formulations. Bowen, 66 JADA 57 (1963); Bowen, U.S. Pat. No. 3,066,112. However, the application of acetone or alcohol to the dentin would be expected to have a desiccating effect analogous to the application of a hypertonic solution, some of which have been shown to cause pain or otherwise insult the pulpal tissues.

2. Description of the Prior Art

U.S. Pat. No. 3,471,927 to Eisenberg teaches the application of, e.g., 20% benzyl alcohol plus 80% isopropanol as a liner in a prepared dental cavity. This mixture does not prevent dehydration of the tooth. The patentee apparently misinterprets the appearance of the treated tooth surface, which is coated by residual benzyl alcohol and does not appear dessicated, as evidence that the surface has not been dehydrated. For is the aromatic alcohol/aliphatic alcohol mixture a mixture of ethylenically unsaturated monomers.

U.S. Pat. No. 2,656,277 to Knappwost teaches the preparation and use of a kind of cement consisting of casein plus calcium oxide and calcium hydroxide, with trace amounts of sodium chloride, potassium chloride, and calcium chloride, which, when mixed with water, will be useful as an "underfilling material for tooth fillings". This cementitious material is not stated to be isotonic, nor is there any evidence given that this property was measured or controlled. The patentee refers to "isotonic blood salt solutions" only in naming the trace salts that are added to his formulation. His cement, as applied to the tooth, is not necessarily isotonic just because the dry powdered casein, calcium oxide, and calcium hydroxide are mixed with an aqueous solution containing chlorides of sodium, potassium, calcium, and magnesium in relative percentages substantially corresponding to hemoisotonic saline fluid. Equally important, it is not an ethylenically unsaturated monomer formulation and does not teach any way in which such a formulation could be made isotonic.

U.S. Pat. No. 4,148,988 to Masuhara et al. teaches a "curable composition" that contains acrylic or methacrylic monomers together with a specific aromatic dibasic acid having an ethylenically unsaturated group, such as 4-methacryloxyethyltrimellitate or its anhydride, related compounds, and mixtures of these. Curable compositions containing these compounds are claimed as a dental adhesive, but there is no teaching or claim of isotonicity or means of obtaining such compositions isotonic with normal physiological saline. One of the principal compounds claimed, the anhydride form of the coupling agent, would be incompatible with water as a composition because it would be hydrolyzed in the presence of water, and for a monomeric composition to be isotonic, it must contain some water.

U.S. Pat. No. 4,102,856 to Lee claims an alicyclic dimethacrylate as a novel component in dental restorative compositions, but teaches no way of making these dimethacrylates isotonic. U.S. Pat. Nos. 3,959,212; 4,150,012; 4,080,212 and 3,539,526 are drawn from related subject matter areas but are less pertinent.

The preparation of ethylenically unsaturated monomer formulations which are substantially isotonic with normal physiological saline solution, and especially their use as vehicles for the application of surface-active comonomers to a dentin surface, have not been described or suggested in any of the prior art. As a consequence, in the process of preparing for application of restorative resins in reconstructive dentistry, injury to dentinal and pulpal tissues has continued. It is with this background that the present invention must be viewed.

SUMMARY OF THE INVENTION

It is an object of this invention to facilitate contact with and adhesion to components of tooth and bone while protecting the tissues from potentially injurious changes in osmotic pressure.

It is also an object of this invention to provide a reproducible means by which the activity of water in liquid ethylenically unsaturated monomer formulations, especially methacrylate and/or acrylate monomer formulations, can be made the same as the activity of water in body tissues.

It is a further object of this invention to present formulations of dental monomers, particularly those containing adhesion-promoting coupling agents, which are osmotically equivalent to 0.9% aqueous sodium chloride.

Other objects of this invention include protection of body tissue surfaces from abstraction or excess application of water (relative to normal homeostatic conditions) during soft tissue replication for scanning electron-micrographic studies, application of prosthetic appliance formulations for dentistry or orthopedic surgery, the use of "bone cements", application of impression-forming materials, and application of adhesive resin formulations, especially if used as vehicles for PolySAC compounds or other adhesion-promoting coupling agents such as NPG-GMA.

These objects are accomplished by application of a composition of matter comprising a solution of water in water-stable ethylenically unsaturated monomers, preferably methacrylate and/or acrylate and most preferably methacrylate monomers, which solution is substantially isotonic with normal physiological saline solution. As a further aspect of the invention, the compositions may be prepared by selecting ethylenically unsaturated monomers of varying hydrophilicity or water solubility, equilibrating each such monomer with water to form a two phase system and measuring the concentration of the monomer in the water-rich phase, preparing a mixture of monomers in equilibrium with water such that their cumulative concentration in the water phase is about 0.31 molar, and collecting the monomer-rich phase, which will be saturated with water and will also be isotonic with normal physiological saline.

It has also been adventitiously discovered that this kind of monomeric solution is a solvent for adhesion-promoting coupling agents such as NPG-GMA or PolySAC compounds, so that the monomeric solution may be employed as a vehicle for the application of surface-active comonomers to a dentin surface.

With the use of isotonic formulations, there is no need to subject bodily tissues, and especially the contents of dentinal tubules, to abnormal osmotic pressures during contacting or application of adhesive formulations.

BRIEF DESCRIPTION OF THE DRAWING

FIG. 1 shows the aqueous solubilities at 37° C. for mixtures of 2-hydroxypropyl methacrylate (HPMA) with triethylene glycol dimethacrylate (TEGD) and of HPMA with 2,2-bis[p(2'-hydroxy-3'-methacryloxypropoxy)phenylene] propane (BIS-GMA).

BRIEF DESCRIPTION OF THE PREFERRED EMBODIMENTS

As indicated, in one aspect the invention is a composition of matter comprising a solution, substantially isotonic with normal physiological saline solution, of water in water-stable ethylenically unsaturated monomers. These monomers are preferably relatively nontoxic.

Generally, ethylenically unsaturated monomers which are polymerizable by free radical polymerization are useful in the instant invention. The term "monomer" as used herein is intended to include prepolymers. Preferred monomers include acrylates and especially methacrylates.

The term "relatively nontoxic" as applied to the ethylenically unsaturated monomers is intended to take into account the balance between the rather small quantity of any individual monomer used at any one time, its systemic toxicity, and its adsorption given the method of its application to tissues. A monomer is relatively nontoxic if it is not unduly toxic under these conditions of use.

An ethylenically unsaturated monomer is, additionally, "water-stable," if it does not react with water and if its free radical polymerization is not inhibited by the presence of water.

The inventive compositions may be prepared as follows.

A quantity of ethylenically unsaturated monomer or other test substance and an equal volume of distilled water are mixed and equilibrated at 37° C. An aliquot of the aqueous phase is withdrawn and its osmotic pressure is measured by appropriate means. Quantitative solute concentrations are computed from a calibration curve. By computation relative to this calibration curve, the concentration of solute particles from any of the unknown solutions can be determined. By this method the solubilities in water of a number of methacrylate monomers ranging in solubilities above and below 0.31 M (the concentration of solute in a normal physiological glucose solution) may be determined.

Next, a monomer having higher than 0.31 mol/l solubility is mixed with one having lower than 0.31 mol/l solubility and the combination is measured for its water solubility. Various proportions are used. From this data, a plot is constructed, and the intersection of the solubility curve with the 0.31 molarity line gives the composition (proportions) having an isotonic concentration in water at 37° C. While theoretically a single monomer may satisfy this criterion, as a practical matter, a mixture of monomers will ordinarily be required.

The resin-rich phase that is in equilibrium with one of these dilute, isotonic, aqueous solutions of monomers is also isotonic, because the chemical potential of water is the same in the supernatent and in the resin-rich phase. In other words, if the supernatant phase of a mixture of monomers equilibrated with water is isotonic, then the other phase is also isotonic because water is in equilibrium with both phases.

More complex formulations may then be developed on the basis of these simple monomer mixtures by the addition of stabilizers and initiators or accelerators. These additives are present in ordinary dental reconstructive resin formulations in relatively small proportions and affect the water solubility only to a small extent. However, if a given trial formulation is not sufficiently soluble in water, an increase in the hydrophilic monomer component can be made.

EXAMPLE I

The materials used in these experiments are listed in Tables 1, 2 and 3. Some of the monomers were not fresh and were not colorless. Nonetheless, it is expected that impurities due to aging probably did not enlarge the experimental error. The concentrations of monomer solutions were calculated on the basis of formula weights, even though it was known that they contained minor amounts of other substances. (Polymerization inhibitors, for example, were known to be present.) HPMA was expected to contain some hydroxypropoxypropyl methacrylate, methacrylic acid, and glycol dimethacrylates in minor amounts, all of which might vary somewhat from one source to another. These impurities were disregarded in the calculations.

TABLE 1

Some of the Less-familiar Materials Used in these Experiments

| Abbreviation | Chemical Name | Source | Reference |
|---|---|---|---|
| BIS-GMA | 2,2-Bis[p-(2'-hydroxy-3'-methacryloxypropoxy)phenyl-ene]propane | Nupol 46-4005; Freeman Chem. Corp.; Port Wash., Wisc. | Bowen, "Properties of a Silica-Reinforced Polymer for Dental Restorations," 66 JADA 57–64 1963). Bowen, U.S. Pat. No. 3,179,623. |
| Barium glass powder | $SiO_2$, 66; BaO, 17; $B_2O_3$, 11; $Al_2O_3$, 6 mol %.* | Code 7724, Corning Glass Works, Corning, N.Y. | Bowen et al., "A New Series of X-Ray-Opaque Reinforcing Fillers for Composite materials, 51 J. Dent. Res. 177–82 (1972). |
| PGD600 | Polyethylene glycol 600 dimethacrylate | Ware Chem. Corp.; Stratford, Conn. | |

*Batch composition

TABLE 2

Solubilities of Monomers in Water at 37° C.

| Methacrylate or dimethacrylate (D) | Abbreviation | Nominal molecular weight | Solubility, molarity |
|---|---|---|---|
| 2-Hydroxyethyl | HEMA | 130 | * |
| Poly(ethylene glycol)600 (D) | PGD600 | 736 | * |
| 4-Hydroxybutyl | HBMA | 158 | 2.44 ± 0.03** |
| 2-Hydroxypropyl | HPMA | 144 | 0.67 ± 0.01 |

TABLE 2-continued

Solubilities of Monomers in Water at 37° C.

| Methacrylate or dimethacrylate (D) | Abbreviation | Nominal molecular weight | Solubility, molarity |
|---|---|---|---|
| Solubility of a nondissociating molecule that gives an isotonic concentration: | | | 0.31 |
| Tetrahydrofurfuryl | THFM | 170 | 0.160 ± 0.003 |
| Tetraethylene glycol (D) | TTGD | 330 | 0.104 ± 0.002 |
| Triethylene glycol (D) | TEGD | 286 | 0.046 ± 0.001 |
| | | | 0.043 ± 0.002*** |
| (See Table 1) (D) | BIS-GMA | 512 | 0.0054 ± 0.003 |
| Ethylene glycol (D) | EGDM | 198 | −0.01**** |
| Methyl | MMA | 100 | −0.03**** |

*Miscible in all proportions.
**The standard deviations represent osmometer replications and do not include errors of batch variability or sample preparation.
***Same source, different lot number.
****A negative value apparently signifies that the solute increases the vapor pressure at 37° C.

TABLE 3

Aqueous Solubilities of Additives Used in Monomer Formulations

| Compound | Abbreviation | Function | Nominal molecular weight | Solubility, molarity |
|---|---|---|---|---|
| Hydroquinone-monomethyl ether | MEHQ | Polymerization inhibitor | 124 | 0.47 ± 0.002 |
| N,N—Bis(2-hydroxyethyl)-p-toluidine | DHPT | Accelerate polymerization | 195 | 0.165 ± 0.001 |
| (See Table 1) | Barium glass powder* | X-ray opaque reinforcing filler | — | 0.056 ± 0.002 |
| Benzoin methyl ether | MEB | Photoinitiate polymerization | 226 | 0.031 ± 0.002 |
| 2-Hydroxy-4-methoxy benzophenone | HMB | UV absorber | 228 | 0.003 ± 0.001 (mp 62C; Cryst./H$_2$O) |
| Benzoyl peroxide | BP | Initiate polymerization | 242 | ** |

*As received; no silane treatment (which would be expected to lower the solubility).
**Negative value; probably a heating or decomposition artifact.

METHODS

About 2 ml of monomer (or experimental formulation) and of freshly distilled water were intimately mixed in a small glass vial, usually by repeatedly aspirating and expelling the mixture with a capillary-tipped disposable glass pipette. Ordinarily, this produced a transient coarse emulsion of the two liquids. The plastic-capped vial was then placed into a chamber maintained at 37° C., at least overnight, for the liquids to separate into two distinct layers and to attain equilibrium miscibility.

An aliquot of the aqueous phase was withdrawn with a disposable capillary pipette, care being taken to avoid obtaining any of the organic liquid phase. This sample was withdrawn immediately after removal from the 37° C. chamber so as to prevent measurable redistribution of the liquids. The sample was immediately placed into a tared vial, covered and weighed. The solution was further diluted with freshly distilled water (usually a ten-fold dilution, by weight) so as to bring the concentration into the optimal range of 0.005 to 0.1 mol/l (moles per liter of solution) for measurement of the solute concentration in a vapor pressure osmometer (Model 302, Mechrolab, Inc., Mountain View, Calif.). The slight inaccuracy of using molarities instead of molalities was not considered significant (relative to other sources of error) in view of the low concentrations and molecular weights of the solutes.

In this instrument, a drop of solution and a drop of solvent (water in this case) were suspended side by side on two small thermistors in a closed chamber saturated with solvent vapor at 37° C. Because of a difference in the vapor pressure of the two drops, a temperature difference developed between them which was proportional to the number of dissolved molecules, ions, or "particles" (solutes of mixed or unknown composition) in the test solution. Quantitative solute concentrations were computed from a linear calibration curve obtained using eight known sodium chloride molarities; the precision of fit was equal to 0.998 in the linear calibration plot. Six osmometer measurements were made for each solution, and the curves were fitted to the averages.

RESULTS

The solubilities of individual monomers in water are given in Table 2. For convenience, these solubilities are expressed in molar rather than molal concentrations as normally used in osmetric pressure relationships.

By combining a monomer having a solubility higher than the isotonic concentration of 0.31 mol/l with one having a solubility lower than this, it was then possible to determine empirically the ratio of a mixture that has a solubility approximating this normal physiological concentration. FIG. 1 illustrates the 37° C. aqueous solubility relationships for mixtures of 2-hydroxypropyl methacrylate (HPMA) and triethylene glycol dimethacrylate (TEGD). Also shown is the curve for HPMA and BIS-GMA binary mixtures. The parabolic curves used to fit the data follow these equations:

(solubility, M)=0.67−0.56 (mol fraction TEGD) −0.07 (mol fraction TEGD)$^2$; and M=0.67−0.92 (mole fraction BIS-GMA +0.26 (mol fraction BIS-GMA)$^2$.

These relationships predict that mixtures of about 60 mol % TEGD plus 40 mol % HPMA or about 45 mol % BIS-GMA plus 55 mol % HPMA will form saturated aqueous solutions at 37° C., the supernatent phases of which are approximately isotonic.

In the resulting systems of one resin-rich phase and one aqueous phase, the chemical potential of water is the same in each phase. That is, the saturation of water in these resin formulations makes them isotonic with normal physiological solutions. The preliminary estimate of the solubility (miscibility) of water in the mixture of 60 mol % TEGD plus 40 mol % HPMA (74.9 wt % TEGD plus 25.1 wt % HPMA) was about 4.5 wt % at 37° C. In the 45 mol % BIS-GMA plus 55 mol % HPMA (74.4 wt % BIS-GMA plus 25.6 wt % HPMA), the water solubility was estimated to be between 5.1 and 5.9% (w/w).

Useful formulations based on such mixtures also require stabilizers, initiators, accelerators, and sometimes other minor additives. These constitute only a few percent of the total composition, and departure of the formulation from "isotonic solubility" should not be large. Nonetheless, these additives were also evaluated for water solubility. See Table 3.

A formulation which contains these and which is approximately isotonic at 37° C. is given in Table 4. This formula is intended to be illustrative only. The BIS-GMA and TEGD are somewhat interchangeable; increasing the BIS-GMA increases the viscosity and decreases the polymerization shrinkage. The concentrations of the stabilizers or polymerization inhibitors (TBSb, BHT, or MEHQ) are probably higher than necessary; if these are lowered, the DHPT and BP might also be reduced somewhat.

TABLE 4

Isotonic Monomer Formulation

| Part A | | Part B | |
|---|---|---|---|
| Ingredient | wt % | Ingredient | wt % |
| HPMA | 40.0 | HPMA | 39.7 |
| BIS-GMA | 34.9 | BIS-GMA | 34.6 |
| TEGD | 15.8 | TEGD | 15.6 |
| Water | 6.78 | Water | 6.00 |
| DHPT | 1.89 | BP | 3.47 |
| TPSb* | 0.32 | TPSb | 0.32 |
| BHT** | 0.20 | BHT | 0.20 |
| MEHQ | 0.11 | MEHQ | 0.11 |

*Triphenyl antimony
**2,6-di-t-butyl-4-methylphenol

Discussion

If each molecular species in the formula were, because of its chemical composition, sufficiently hydrophilic to be soluble in water to the extent of exactly 0.31 mol/l, then there would be more convenience and freedom in the process of formulation of isotonic methacrylate and/or acrylate compositions. However, because of the colligative nature of osmotic pressure, it is not necessary that each ingredient have this specific water solubility, only that the overall formulation have a solubility that provides an equilibrium solute concentration of 0.31 mol/l in water at 37° C. The water saturated formulation is then also isotonic. The subject of the relative molecular weights of the components as they may affect osmotic pressure has not been dealt with specifically. The upper limits of molecular weight will be set by viscosity, handling characteristics, and solubility in the other components. The lower limits should be avoided, a priori, to minimize volatility, hardening shrinkage, and untoward tissue penetration and toxicity.

For chemical adhesion to dentin (or other substrates that contain hydrated surface layers or residual surface water), an isotonic monomer formulation could be reduced slightly in its computed water content (empirically) by the amount of water that must be taken up by it from the surface. The formulation would then remain substantially isotonic, although deficient in the small amount of moisture contained on the substrate surface; the formulation could then absorb this slight amount of moisture, thereby becoming fully isotonic. The extent to which the composition becomes a "hygroscopic formulation" (by reduction of its water content) should be restricted to prevent hypertonic effects on contiguous vital tissues and excessive expansion due to subsequent water sorption from the environment.

Monomer formulations, which would be isotonic if saturated with water, minus somewhat more of their water content, may be useful as sealant resins for developmental pits and fissures in enamel, as opposed to dentin, for two reasons: They may penetrate more deeply because they can sorb or dissolve some of the residual water trapped in the pit, fissure, or enamel pores, and the subsequent volumetric hygroscopic expansion might compensate for polymerization shrinkage and thereby help retain them in these surface voids.

Alternative means are available for preparation of the isotonic monomer compositions. Essential to the procedure is some means of measuring the concentration of "particles" of solute in complex aqueous solutions of unknown concentrations. Because osmotic pressure is a colligative property, it is concerned only with the amount of dissolved substances and not with the kind. Therefore, there might be a number of different methods for measuring the osmotic pressure of monomers in water that would be suitable for preparing isotonic monomer formulations. Less hydrophilic monomer formulations which contain smaller amounts of water than shown in Table 4 can be prepared in isotonic form by equilibrating the monomers with, for example, a physiological saline solution (0.9% NaCl), provided that the latter is in very large excess or is "titrated" with water to maintains its isotonicity during the water exchange and provided that all solutes remain in their initial phases (i.e., only water is allowed to cross a semipermeable membrane separating them).

The apparently less-than-zero solubility values for MMA and EGDM (Table 2) and for methanol, ethanol, and acetone (not shown) suggest that in spite of their solubility in water they increase the vapor pressure of their solutions at 37° C. This could suggest that their molecular weights and molar volumes might be low enough to let such molecules penetrate tissue membranes and structures more than could similar but larger molecules. The "pores" in odontoblastic cell membranes are doubtlessly not like those of ideal semipermeable membranes; these and other vital tissues must be permeable (passively as well as by active transport) to aqueous solutes of various sizes. But is is reasonable to assume, until more specific information is available, that "foreign" compounds (such as most of the solutes in these examples) could penetrate tissues in some manner related to their vapor pressures or molecular size. MMA resin restorations have been associated with unfavorable pulp responses, which, according to this reasoning, may not be due altogether to "percolation" and their other physical imperfections. Nelson et al., "Fluid Exchange in the Margins of Dental Restorations," 44 JADA 288 (1952); Paffenbarger et al., "Direct and Indirect Filling Resins: A Review of Some Physical and Chemical Properties," 47 JADA 516 (1953).

These isotonic monomer formulations are preferably employed as vehicles for surface-active comonomers to be applied as adhesive resin "liners" on cleaned and mordanted dentin under composite restorative materials. However, some isotonic monomer formulations per se may be inherently more adhesive then divergent formulations, because the ratio of polar and nonpolar group may be more similar to the balance of polar and nonpolar components constituting the surfaces of biological tissues. This relationship can be contemplated in terms of "compatibility," cohesive energy density, solubility parameter, or "wetting" often discussed in adhesion technology.

EXAMPLE II

Isotonic monomer formulations contain about 4 to 7 % water by weight and are more polar than ordinary BIS-GMA formulations. It is probably for that reason that the isotonic monomers are fairly good solvents for surface-active comonomers such as NPG-GMA and PolySAC compounds. This example illustrates use of an isotonic monomer formulation as a vehicle for application of surface-active comonomers.

A provisional two-component formulation containing NPG-GMA (which serves the dual role of adhesion-promoter and polymerization accelerator) in the first component and containing benzoyl peroxide (a polymerization initiator) in the second component were compounded and the compositions are given in Tables 5 and 6. (The formulation was prepared in two components to keep separate the polymerization initiator and the accelerator until reaction was desired.) The proportions of the various ingredients are approximated, because even the same monomer coming from different manufacturers or as different batches from the same supplier gave slightly different water solubilities and would therefore affect the optimum proportions of a complete formulation. Furthermore, many other formulations with other hydrophilic and hydrophobic monomers can be isotonic.

Preliminary adhesion tests with dentin have been performed using the formulation of Table 5; a thin film of part A was applied before one of part B. The strength of the bonds between this surface and a composite averaged higher than those when the composite was placed directly on the dentin. See Table 7.

It should be understood that the foregoing disclosure emphasizes certain specific embodiments of the invention and that all modifications or alternatives equivalent thereto are within the spirit or scope of the invention as set forth in the appended claims.

TABLE 5

| Isotonic Adhesive Resin Formulation | | | |
|---|---|---|---|
| Part A | | Part B | |
| Ingredient* | wt % | Ingredient* | wt % |
| HPMA | 40.0 | HPMA | 40.0 |
| BIS-GMA | 34.9 | BIS-GMA | 34.7 |
| TEGD | 15.8 | TEGD | 15.6 |
| Water | 6.8 | Water | 6.0 |
| NPG-GMA** | 2.18 | BP** | 3.5 |
| TPSb | 0.16 | TPSb | 0.16 |
| BHT | 0.10 | BHT | 0.03 |
| MEHQ | 0.06 | MEHQ | 0.01 |

*Abbreviations are defined in Table 6.
**Storage stability of monomeric solutions containing NPG-GMA or BP is limited. These ingredients should be added shortly before use, and adequate atmospheric oxygen must be available as a co-stabilizer.

TABLE 6

| Components Listed in Table 5 | | | |
|---|---|---|---|
| Abbreviation | Name | Nominal molecular weight | Solubility in water at 37° C., mol/L |
| HPMA | 2-Hydroxypropyl methacrylate | 144 | 0.67 |
| BIS-GMA | 2,2-Bis[p-2'-hydroxy-3'-methacryloxy propoxy) phenylene] propane | 512 | 0.005 |
| TEGD | Triethylene glycol dimethacrylate | 286 | 0.044 |
| NPG-GMA | N—(2-hydroxy-3-methacryloxypropyl)-N—phenylglycine | 295 | 0.019 |
| TBSb | Triphenyl antimony | 353 | 0.004 |
| BHT | 2,6-Di-(t-butyl)-4-methylphenol | 220 | 0.0008 |
| MEHQ | Hydroquinonemonomethyl ether | 124 | 0.47 |

TABLE 7

Improved Adhesion Between a Composite and Dentin from the Use of an Isotonic Cleanser, an Isotonic Mordant, and an Isotonic Resin Formulation

| Cleanser | Mordant | Resin | Average Adhesion, kPa* | Standard Deviation (range) |
|---|---|---|---|---|
| Water | Water | None | 21 | 41 (0–83) |
| Isotonic formic acid | Isotonic zinc chloride | None | 110 | 180 (0–480) |
| Isotonic formic acid | Isotonic zinc chloride | Table 5 formulation** | 1,900 | 1,100 (830–4,300) |

*Average of 9 measurements.
**Except that the stabilizer concentrations were somewhat lower.

What is claimed is:

1. A composition of matter comprising a solution, substantially isotonic with normal physiological saline solution, of water in water-stable ethylenically unsaturated monomers.

2. A composition of matter comprising a solution of water in water-stable ethylenically unsaturated monomers wherein the osmotic pressure of the solution substantially equals the osmotic pressure of an aqueous 0.31 mole per liter glucose solution.

3. A composition of matter as in claim 1 or 2 wherein the ethylenically unsaturated monomers are selected from the group consisting of methacrylates and acrylates.

4. A composition of matter as in claim 3 wherein the ethylenically unsaturated monomers are methacrylates.

5. A composition of matter as in claim 1 or wherein the ethylenically unsaturated monomers are relatively nontoxic.

6. A composition of matter comprising a solution of water in relatively nontoxic water-stable ethylenically unsaturated monomers which is substantially osmotically equivalent to 0.9 percent by weight aqueous sodium chloride.

7. An isotonic monomer formulation, useful as a vehicle for the application of adhesion-promoting surface-active comonomers to the surface of dentin, comprising a composition of matter as in claim 1.

8. An isotonic monomer formulation, useful as a vehicle for the application of adhesion-promoting surface-active comonomers to the surface of dentin, comprising a composition of matter as in claim 3.

9. An isotonic monomer formulation, useful as a vehicle for the application of adhesion-promoting surface-active comonomers to the surface of dentin, comprising a composition of matter as in claim 4.

10. An isotonic monomer formulation as in claim 7 comprising a saturated solution of water in a mixture of about 60 mole percent triethylene glycol dimethacrylate and about 40 mole percent 2-hydroxypropyl methacrylate.

11. An isotonic monomer formulation as in claim 7 comprising a saturated solution of water in a mixture of about 45 mole percent 2,2-bis[p-(2'-hydroxy-3'-methacryloxypropoxy)phenylene]propane and about 55 mole percent 2-hydroxy propyl methacrylate.

12. An isotonic monomer formulation as in claim 7 further comprising one or more additives selected from the group consisting of stabilizers, initiators and accelerators.

13. An isotonic monomer formulation as in claim 12 comprising a saturated solution of water in a mixture of about 40 weight percent 2-hydroxypropyl methacrylate, about 35 weight percent 2,2-bis[p-(2'-hydroxy-3'-methacryloxypropoxy)phenylene]propane, and about 16 weight percent triethylene glycol dimethacrylate, also containing triphenyl antimony as a stabilizer, 2,6-di-t-butyl-4-methylphenol as a stabilizer, hydroquinonemonomethylether as a stabilizer, benzoyl peroxide as an initiator, and DHPT as an accelerator.

14. A composition of matter comprising a mixture of an isotonic monomer formulation as in claim 7 with at least one adhesion-promoting surface-active comonomer.

15. A composition of matter as in claim 14 wherein the adhesion-promoting surface active comonomer is selected from the group consisting of N-(2-hydroxy-3-methacryloxypropyl)-N-phenylglycine and polyfunctional surface active comonomers.

16. A composition of matter as in claim 15 comprising a saturated solution of water in a mixture of about 40 weight percent 2-hydroxypropyl methacrylate, about 35 weight percent 2,2-bis[p-(2'-hydroxy-3'-methacryloxypropoxy)phenylene]propane, about 16 weight percent triethylene glycol dimethacrylate, and about 2% N-(2-hydroxy-3-methacryloxypropyl)-N-phenylglycine.

17. An isotonic monomer formulation, useful for the protection of body tissues from abstraction or excess application of water, relative to normal homeostatic conditions, during soft tissue replication for scanning electron-micrographic studies, comprising a composition of matter as in claim 1.

18. An isotonic monomer formulation, useful for the protection of body tissues from abstraction or excess application of water, relative to normal homeostatic conditions, during application of prosthetic applicance formulations for dentistry or orthopedic surgery, comprising a composition of matter as claimed in claim 1.

19. An isotonic monomer formulation, useful for the protection of body tissues from abstraction or excess application of water, relative to normal homeostatic conditions, during application of bone cement, comprising a composition of matter as claimed in claim 1.

20. An isotonic monomer formulation, useful for the protection of body tissues from abstraction or excess application of water, relative to normal homeostatic conditions, during application of impression-forming materials to soft tissues, comprising a composition of matter as in claim 1.

* * * * *

UNITED STATES PATENT AND TRADEMARK OFFICE
CERTIFICATE OF CORRECTION

PATENT NO.  : 4,373,035
DATED       : February 8, 1983
INVENTOR(S) : Rafael L. Bowen It is certified that error appears in the above-identified patent and that said Letters Patent is hereby corrected as shown below:

After "BACKGROUND OF THE INVENTION" and before the first line of the specification insert:

--The invention described herein was made in the course of work under a grant or award from the DEPARTMENT of Health, Education and Welfare.--

Signed and Sealed this

Sixth Day of September 1983

[SEAL]

*Attest:*

*Attesting Officer*

GERALD J. MOSSINGHOFF

*Commissioner of Patents and Trademarks*